Figure 1:
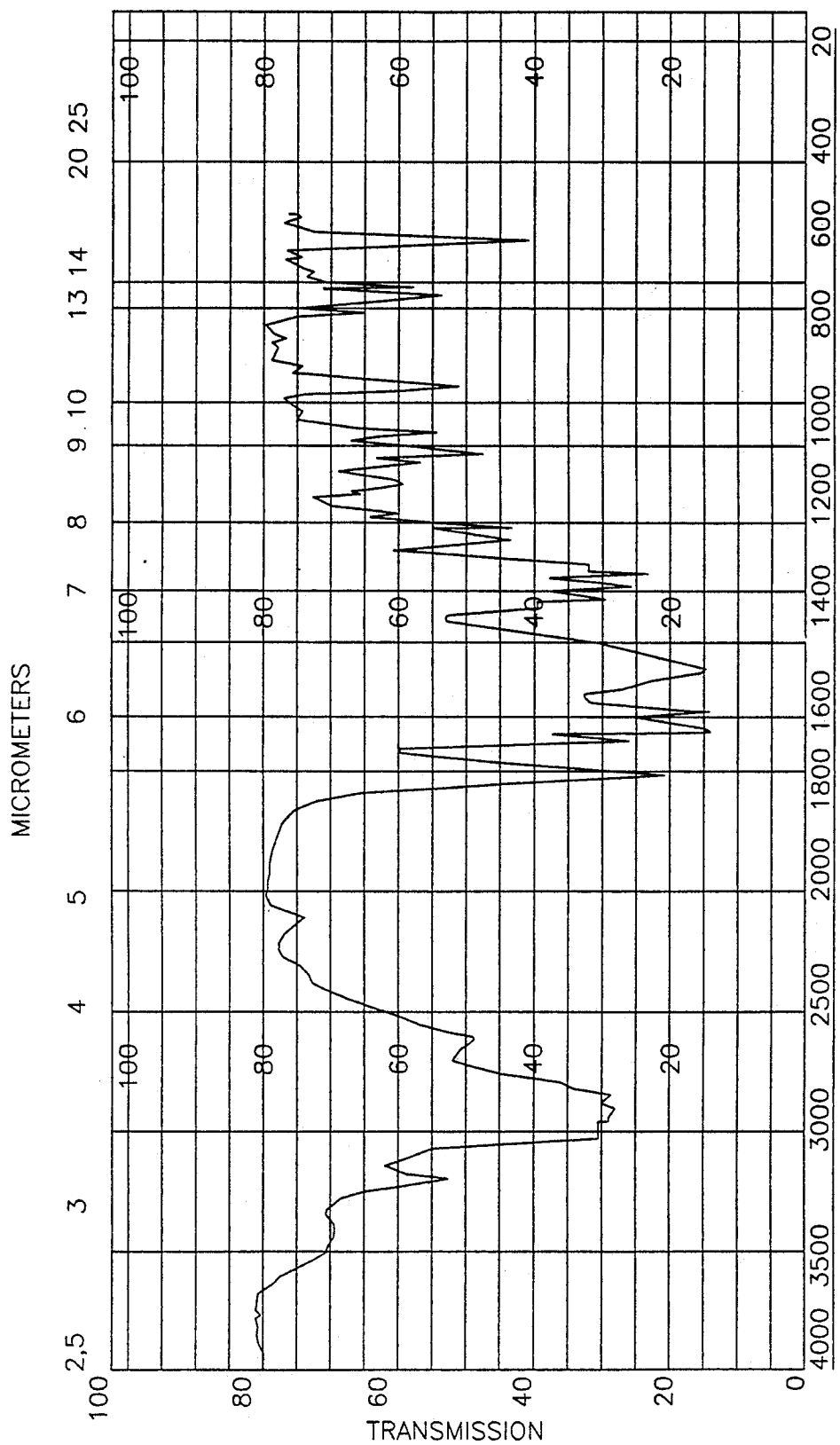

United States Patent [19]

Meseguer et al.

[11] Patent Number: 5,278,157
[45] Date of Patent: Jan. 11, 1994

[54] STABLE CEPHRADINE HYDRATE

[75] Inventors: Jose D. Meseguer, Granollers; Rafael B. Codes; Santiago A. Ciriza, both of Barcelona, all of Spain

[73] Assignee: GeMa, S.A., Barcelona, Spain

[21] Appl. No.: 755,251

[22] Filed: Sep. 5, 1991

Related U.S. Application Data

[63] Continuation of Ser. No. 554,602, Jul. 18, 1990, abandoned, which is a continuation-in-part of Ser. No. 377,668, Jul. 10, 1989, abandoned.

[51] Int. Cl.$^5$ .................. C07D 501/22; A61K 31/545
[52] U.S. Cl. ..................................... 514/209; 540/230
[58] Field of Search ................. 540/230, 228; 514/209

[56] References Cited

U.S. PATENT DOCUMENTS

| 3,485,819 | 12/1969 | Weisenborn et al. | 260/239.1 |
| 3,502,663 | 3/1970 | Barnes | 260/243 |
| 3,819,620 | 6/1974 | Dürsch et al. | 260/243 C |

FOREIGN PATENT DOCUMENTS 777789 1/1972 Belgium .

OTHER PUBLICATIONS

Analytical Profiles of Drug Substances vol. 5 Edited by Klaus Florey (1976) pp. 37–45.

*Primary Examiner*—Nicholas S. Rizzo
*Attorney, Agent, or Firm*—Robert S. Honor; Melvyn M. Kassenoff; Thomas O. McGovern

[57] ABSTRACT

The invention relates to a novel stable form of cephradine, processes for its production and intermediates used therein.

11 Claims, 4 Drawing Sheets

STABLE CEPHRADINE HYDRATE

This is a continuation application Ser. No. 07/554,602, filed Jul. 18, 1990, now abandoned which in turn is a continuation-in-part of application Ser. No. 07/377,668, filed Jul. 10, 1989, now abandoned.

This invention relates to the known, commercially available, antibiotic cephradine. Cephradine is the International Non-Proprietary Name of the compound 7-[D-2-amino-2-(1,4-cyclohexadienyl)acetamido]-desacetoxycephalosporanic acid of formula I.

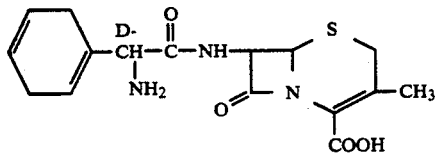

Cephradine was first described in the late 60's and various processes for its production have been described. There is considerable evidence that the product exhibits polymorphism and indeed four polymorphs have been described [Analytical Profiles of Drug Substances, Volume 5, 37-43 (1976)]. For various reasons, the commercially available form is a hydrated form in which the water content is in the range of about 3% to about 6% per weight. This is not a stoichiometric hydrate since the water varies freely in the crystal. The inherent problem with this commercially available form is its poor stability. Thus, it is prone to oxidation to cephalexin (the corresponding product in which the cyclohexadienyl ring is replaced by a benzene ring), to degradation and to coloration. It also has a low bulk density which is a disadvantage since the form is also prone to degradation upon compacting.

U.S. Pat. No. 3,819,620 describes a dihydrate form of cephradine. This form is reported to have a substantially higher bulk density than the hydrated form referred to above and to be substantially more stable (Analytical Profiles of Drug Substances, ibid.). However, it is difficult and expensive to obtain and it is presumably for this and other reasons that this form has not become commercially available.

Belgian Patent 777,789, in the name of Eli Lilly, quite generally describes dimethylformamide complexes of cephalosporins. However, it makes no reference to cephradine and is primarily concerned with α-aminophenylacetamido-desacetoxycephalosporanic acids such as cephalexin and p-hydroxycephalexin (now known as cefadroxil).

It is an object of the present invention to provide a novel stable form of cephradine hydrate, hereinafter referred to as a cephradine SF (stable form). The present invention also provides a novel intermediate in the production of cephradine, namely cephradine dimethylformamide solvate. The present invention finally provides a process for producing cephradine SF.

FIG. 1 is the IR spectra of cephradine dimethylformamide solvate.

Figure 2:
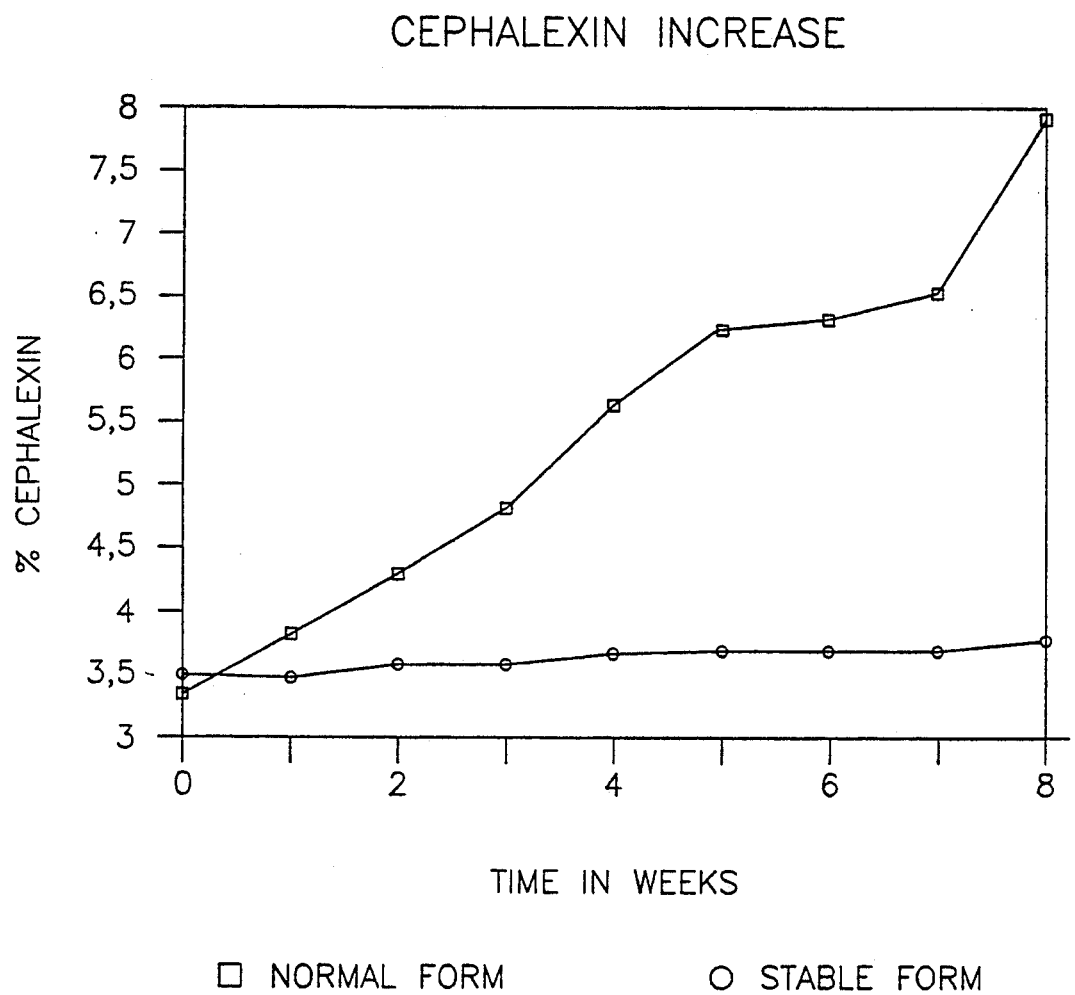
Figure 3:
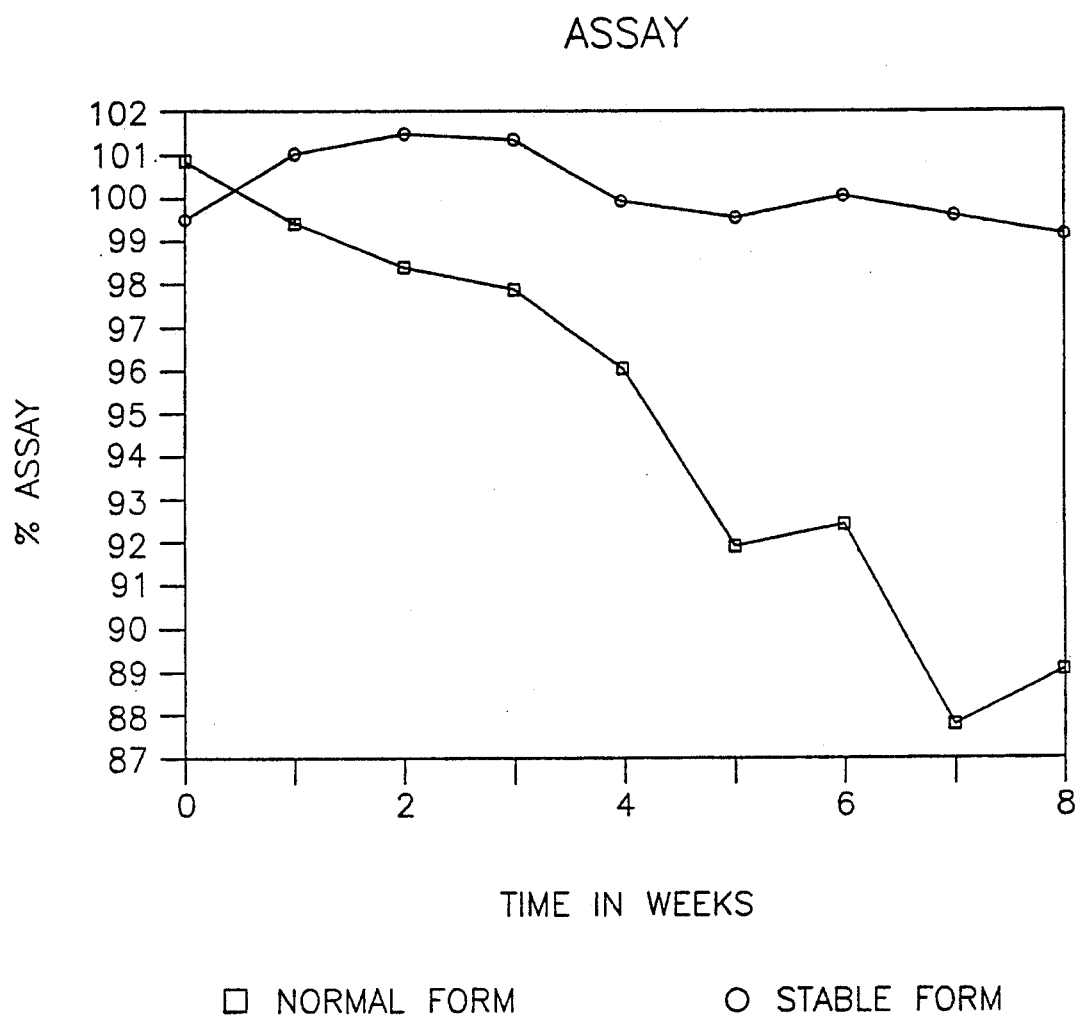
Figure 4:
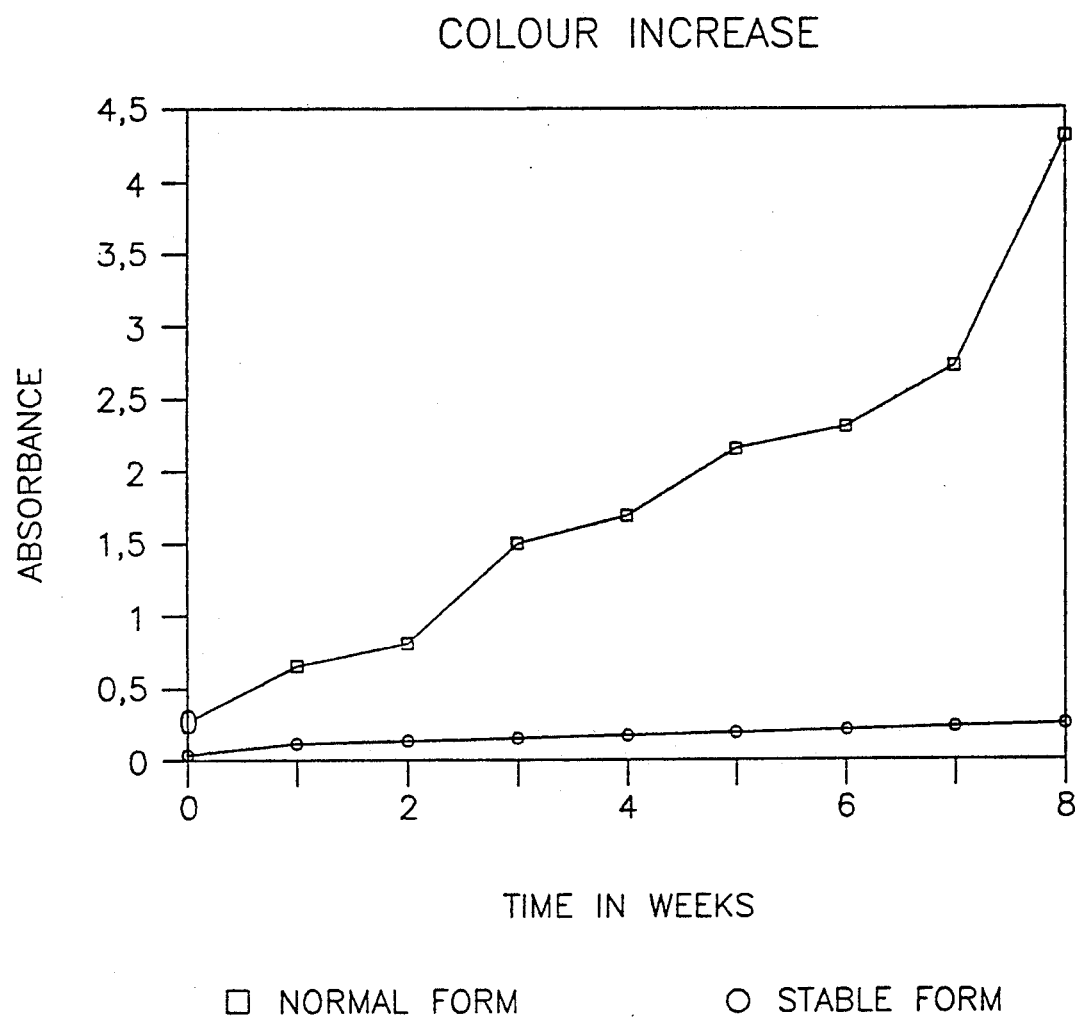

FIGS. 2, 3, and 4 are the cephalexin content, cephradine assay, and color increase respectively for stability comparisons between cephradine SF and commercial cephradine.

The cephradine SF of the present invention has essentially the same IR spectrum and a similar or essentially the same X-ray diffraction pattern to the commercially available form of cephradine hydrate referred to above. It also has a water content within the limits specified in the United States Pharmacopoeia for the non-stoichiometric "monohydrate", namely not more than 6% by weight as determined by Karl Fischer analysis and is therefore quite distinct from the previously reported dihydrate. More typically the cephradine SF of the invention has a water content of from about 3 to about 6%, preferably about 3.5% to about 4.5%, by weight.

However, the cephradine SF of the present invention differs in several very important characteristics.

Firstly, the crystals are much larger, and normally are approximately double the size. Apparently, as a result the bulk density is far higher and its tapped density prior to any milling or other particle size reduction procedures is normally at least or other particle size reduction procedures is normally at least 0.5 g/ml, and is more usually at least 0.7 g/ml, e.g. 0.7 to 0.8 g/ml and more particularly from 0.75 to 0.8 g/ml, typically from 0.75 to 0.77 g/ml, as compared to the average tapped density of the commercially available hydrate ("monohydrate") form of about 0.45 g/ml. This is important since the cephradine SF of the invention as a result does not require a compacting step for its formulation.

"Tapped Density" as herein refers to density at constant volume and is suitably determined by the following method: approximately 70 to 90 ml of the material (whose tapped density is to be determined) is added to a graduated 100 ml cylinder through a plastic funnel and the bulk volume of the material is read and recorded. The cylinder is placed in a tapping apparatus (e.g. STAV 2003) and is subjected to 1000 taps. The resulting volume is then read and recorded to give the tapped volume. The weight of the material is divided by the tapped volume to give the tapped density.

The cephradine SF of the invention is also much more stable than the commercially available hydrate ("monohydrate") form as determined by conventional stability tests on, for example, coloration. Thus, while commercial forms of cephradine monohydrate show a substantial increase of coloration when subjected in a closed container to an environment maintained at 40° C. and 70% relative humidity for a period of at least 8 weeks (hereinafter referred to as "closed Stress Stability test"), the coloration of the cephradine SF of the invention remains essentially the same. By this is meant that the absorbance (as explained hereinafter) at 450 nm, using sodium carbonate as blank, after the stress test is with the cephradine SF of the invention less than 1, more particularly less than 0.5, more particularly less than 0.2 after 4 weeks. Even after 8 weeks, the absorbance is still less than 1 typically under 0.5, more particularly under 0.3. In contrast, commercially available cephradine monohydrate shows an absorbance of usually over 1 at four weeks and from 3 to 5 at 8 weeks whether in the closed stress stability test.

In addition, the surprisingly increased stability of the cephradine SF according to the invention is demonstrated by its essentially unchanged cephalexin content when subjected to the same closed stress stability test. In particular, the cephalexin content of the cephradine SF of the invention increases no more than 20%, more typically no more than 15% and usually no more than about 10% by weight after 4 weeks or even 8 weeks of such stress stability conditions. In contrast, commercially available cephradine monohydrate will approximately double in cephalexin content after 8 weeks.

The cephradine SF of the present invention also appears to be less inclined to absorb water upon standing in the atmosphere at room temperature.

The advantages of the cephradine SF of the invention are substantial in terms of ease of formulation and shelf-life. Moreover, the cephradine SF of the invention can be produced in an economic manner in contrast, apparently, to the previously reported, stable dihydrate.

In accordance with the invention, cephradine SF is produced by crystallisation from an aqueous dimethylformamide solution of cephradine.

In one aspect the present invention provides a process for the production of cephradine hydrate comprising preparing an aqueous dimethylformamide solution of cephradine and crystallising the cephradine hydrate therefrom. The cephradine SF may be isolated by e.g. conventional procedures in beta-lactam chemistry. Crystallisation may be effected e.g. by preparing a super-saturated solution e.g. by pH adjustment and by cooling.

The cephradine used as starting material may be produced by any method for its production and may be in any form. For example, it may be in salt form, such as hydrochloride salt form, or indeed may be in known hydrated forms. In any event, an aqueous solution of the cephradine starting material is preferably first formed, for example by dissolution in aqueous hydrochloric acid at e.g. 5° to 10° C. and, if desired or required, the pH may be adjusted to pH 1.5 to 2.5, for example by addition of hydrochloric acid for this purpose. Dimethylformamide is then suitably added to the solution. The quantity of dimethylformamide to be added is conveniently about 1/20 to about 1/5 of the volume of the aqueous layer. The mixture may then be filtered and washed, e.g. with water. The solution is then preferably brought to about 35° to 40° and is then suitably adjusted to a pH of from about 2.4 to 2.8 with a base, such as ammonia, sodium hydroxide or triethylamine at which crystallisation starts. The pH is then preferably adjusted to about 4.7 to 5.1. The resulting suspension is then preferably cooled to a temperature of about 15° to 25° C. and filtered. The resulting residue may, if desired be washed with an organic solvent, such as acetone, to obtain cephradine SF of the invention.

In another aspect the present invention provides a process for the production of cephradine hydrate which comprises crystallising said hydrate from an aqueous solution of cephradine dimethylformamide solvate.

Thus the cephradine dimethylformamide solvate resulting from addition of the dimethylformamide to the aqueous cephradine solution may be isolated and optionally purified prior to further processing. The DMF solvate may be produced in accordance with the invention by treating an aqueous solution of cephradine with dimethylformamide at a temperature of less than about 35° C. more usually about 5° to 15° C. The quantity of dimethylformamide to be added may vary within fairly wide limits but in general the volume to be added is one to at least several times the volume of the aqueous layer. The precipitation is preferably accomplished by adjusting the pH of the mixture to about 6.3 to 7.3 by addition of a base, such as ammonia, sodium hydroxide or triethylamine, at for example 30° to 35° C. whereupon precipitation begins. The resulting mixture is suitably cooled to about 15° to 25° C. and filtered. The resulting DMF solvate may be optionally purified in conventional manner.

The dimethylformamide solvate obtained as described above may then be dissolved in aqueous hydrochloric acid at e.g. 5° to 10° C. and, if desired or required, the pH may be adjusted to pH 1.5 to 2.5, for example by addition of hydrochloric acid for this purpose. The mixture may then be filtered and washed, e.g. with water. The solution is then preferably brought to about 35° to 40° C. and is then suitably adjusted to a pH of from about 2.4 to 2.8 with a base, such as ammonia, sodium hydroxide or triethylamine at which crystallisation starts. The pH is then preferably adjusted to about 4.7 to 5.1. The resulting suspension is then preferably cooled to a temperature of about 15° to 25° C. and filtered. The resulting residue may, if desired be washed with an organic solvent, such as acetone, to obtain cephradine SF of the invention.

The cephradine dimethylformamide solvate described above is new and also forms part of the present invention. It may comprise from at least 0.5, preferably 0.5 to 10, more preferably 0.5 to 3, most preferably about 0.75 to 2.5 moles of dimethylformamide per mole of cephradine. In a preferred embodiment, it contains about 1.00 to about 2 moles of DMF per mole of cephradine, e.g. about 1.5 moles of DMF per mole of cephradine.

In a particularly preferred embodiment it contains from 1.8 to 2.2 moles of DMF per mole of cephradine, especially about 2 moles of DMF per mole of cephradine.

The cephradine SF of the invention may be used in the same manner and, at the doses and in the same indications as for cephradine. The cephradine SF may be worked up into pharmaceutical compositions.

In another aspect the present invention provides a pharmaceutical composition containing cephradine SF in association with a pharmaceutical carrier or diluent, as well as processes for their production.

Such compositions may be for example in the form of capsules, tablets, injectable solutions and suspensions. The compositions may contain from about 0.1 to about 99.9% by weight of cephradine SF.

The following Examples, in which all temperatures are in degrees Centigrade illustrate the invention.

EXAMPLE 1 CEPHRADINE STABLE FORM (SF)

a) Cephradine Dimethylformamide Solvate

To an aqueous solution of about 270 ml, containing approximately 49 g of cephradine in the form of its hydrochloride, (and obtained, after extraction from any suitable reaction mixture of cephradine) 340 ml of dimethylformamide were added, the temperature being maintained at below 35°. The pH was adjusted to 4.3 by addition of ammonia at 30°–35° C. and the mixture was stirred for several minutes as precipitation commenced. The pH was further adjusted to 6.6 with ammonia at 30° to 35° and the slurry was then cooled to 20° to 25° and filtered. The cake was washed with 160 ml of DMF and 130 ml of acetone to obtain the heading compound.

MP: approx. 160° to 164°
Analysis: (by weight)
  Cephradine=70.6%
  Cephalexin=1.7%
  Water=0.5%
  DMF=25 to 30%
IR: FIG. 1 b) Cephradine SF 125 g of cephradine dimethylformamide solvate (as for example produced in step a) above) were suspended in water/conc. HCl (300/12.5) at 5° to 10° C. with stirring. The pH was adjusted to 1.6 to 2.0 by addition of hydrochloric acid in order to obtain a complete solution. The solution was filtered and the residue washed with 60 ml of water. The combined filtrate was warmed to 35° to 40° C. The pH was adjusted to 2.4 to 2.8 with triethylamine whereupon precipitation started. The stirring was maintained for several minutes. The pH was then adjusted to 4.7 to 5.1 with triethylamine and the suspension was cooled to about 25° and filtered. The residue was washed with 270 g of acetone (80% v/v) to obtain the heading compound, m.p. 190° to 200° C. (decomp.).

EXAMPLE 2 CEPHRADINE STABLE FORM (SF)

Example 1 is repeated using in place of ammonia at each instance in step a) the required amount of either sodium hydroxide or triethylamine to bring the pH to that indicated. Cephradine dimethylformamide solvate and the heading compound are likewise obtained.

EXAMPLE 3 CEPHRADINE STABLE FORM (SF)

50 g of commercially available cephradine hydrate were suspended in a mixture of water and conc. hydrochloric acid (180/7) at 5° to 10° C. with stirring. The pH was brought to 1.6 to 2.0 with hydrochloric acid in order to form a complete solution and 16 g of dimethylformamide were added. The solution was filtered and the residue was washed with 35 ml of water. The combined filtrate was warmed to 35° to 40° and the pH brought to 2.8 with aqueous triethylamine. Stirring was continued for several minutes and the pH was finally adjusted to about 4.9 with aqueous triethylamine. The resulting slurry was cooled to room temperature and filtered. The residue was washed with 80% (v/v) acetone and dried to obtain the heading compound, m.p. 190° to 200° C. (decomp.).

EXAMPLE 4 ANALYTICAL DATA OF CEPHRADINE SF VS COMMERCIAL CEPHRADINE HYDRATE

A batch of commercially available cephradine hydrate and a batch of Cephradine SF were subjected to the following stress stability test: about 5 kgs of product, kept in a commercial container in a climatic room at 40° C. and 70% relative humidity for 8 weeks. At weekly intervals the batches were analysed inter alia for cephalexin content, assay and colour increase using conventional procedures described below. The results are summarised in FIGS. 2, 3 and 4. It will be seen that the cephradine SF of the invention is remarkably stable, judged by any of these parameters, over the 8 week period while the normal commercially available hydrate deteriorates seriously.

CEPHALEXIN CONTENT: PROCEDURE

Equipment: Hewlett-Packard chromatograph 1084 B or similar.
Detector: U.V. at 254 nm.
Column: RP-8 (Hypersil MOS), 10 cm, 5 μm or equivalent.
Mobil phase: Phosphate buffer 20 mM., pH 5.0/Methanol (75/25).
Temperature: 40° C.
Flow: 1.5 ml/min.
Injection: 20 μl.
Retention time—120 sec.

$$\% = \frac{VI_M \times W_{st} \times 100}{VI_{st} \times W_M \times (100 - H_M)} \times A_{st}$$

$W_{st}$: Concentration of standard
$W_M$: Concentration of sample
$H_M$: Moisture of sample
$A_{st}$: Potency of standard (as is)
$VI_M$: Integration value of the cephalexin peak (sample)
$VI_{st}$: Integration value of the cephalexin peak (standard)

Solution:
a) Phosphate buffer 20 mM., pH 5.0
Weight 2.72 g of $KH_2PO_4$ and dissolve in 1.000 ml of water
b) Cephalexin standard
Disolve 100 mg, exactly weighed, in 50 ml of phosphate buffer. Take 1 ml. and complete to 25 ml with the same buffer.
c) Sample
Dissolve 100 mg, exactly weighed, in 50 ml of phosphate buffer.

ASSAY: HPLC PROCEDURE

Equipment: Hewlett-Packard chromatograph 1084 B or similar.
Detector: U.V. at 254 nm.
Column: RP-8 (Hypersil MOS), 10 cm, 5 μm or equivalent.
Mobil phase: Phosphate buffer 20 mM., pH 5.0/Methanol (75/25).
Temperature: 40° C.
Flow: 1.5 ml/min.
Injection: 5 μl.
Retention time—150 sec.

$$\% = \frac{VI_M \times W_{st} \times 100}{VI_{st} \times W_M \times (100 - H_M)} \times A_{st}$$

$W_{st}$: Weight of standard
$W_M$: Weight of sample
$H_M$: Moisture of the sample
$A_{st}$: Potency of standard (as is)
$VI_M$: Integration value of the cephradine peak (sample)
$VI_{st}$: Integration value of the cephradine peak (standard)

Solutions:
a) Phosphate buffer 20 mM., pH 5.0.
Weight 2.72 g of $KH_2PO_4$ and dissolve in 1.000 ml of water.
b) Cephradine standard
Dissolve 100 mg, exactly weighed, in 50 ml of phosphate buffer.
c) Sample
Dissolve 100 mg, exactly weighed, in 50 ml of phosphate buffer.

COLORATION: PROCEDURE

Dissolve 2 g of product in 10 ml of 10% w/v of sodium carbonate. Read the absorbance at 450 nm., using sodium carbonate as blank.

TAPPED DENSITY

The tapped density of the commercially available cephradine hydrate has an average value of 0.45 g/ml. The tapped density of cephradine SF is 0.75 g/ml.

What is claimed is:

1. A stable cephradine hydrate having a water content (Karl-Fischer) of from about 3 to about 6% by weight and a tapped density of at least 0.5 g/ml.

2. Cephradine hydrate of claim 1 having a tapped density of at least 0.7 g/ml.

3. Cephradine hydrate of claim 1 having a tapped density of from 0.7 to 0.8 g/ml.

4. Cephradine hydrate of claim 1 having a water content (Karl-Fischer) of from about 3 to about 6% by weight, which shows no substantial increase in coloration when kept in a closed container in an environment maintained at 40° C. and 70% relative humidity over a period of 8 weeks.

5. Cephradine hydrate of claim 4, which shows absorbance at 450 nm of less than 1 after said 8 weeks.

6. Cephradine hydrate of claim 1, having a water content (Karl-Fischer) of from about 3 to about 6% by weight, which shows an increase in cephalexin content of no greater than 20% by weight when kept in a closed container in an environment maintained at 40° C. and 70% relative humidity over a period of 8 weeks.

7. A process for the production of cephradine hydrate comprising preparing an aqueous dimethylformamide solution of cephradine and crystallising the cephradine hydrate therefrom.

8. A process for the production of cephradine hydrate which comprises crystallising cephradine hydrate from an aqueous solution of cephradine dimethylformamide solvate.

9. A pharmaceutical composition comprising a therapeutically effective amount of cephradine hydrate according to claim 1 in association with a pharmaceutical carrier or diluent.

10. A process according to claim 7, which comprises dissolving cephradine or a salt form thereof in an aqueous acid solution at a temperature of 5° to 10° C.; adjusting the pH to 1.5 to 2.5; adding 1/20 to 1/5 the volume of the aqueous solution of dimethylformamide; heating to 35° to 40° C.; adjusting the pH to 2.4 to 2.8 and then to 4.7 to 5.1; cooling to 15° to 25° C.; and recovering the cephradine hydrate obtained.

11. A process according to claim 8, which comprises dissolving cephradine dimethylformamide solvate in an aqueous acid solution at a temperature of 5° to 10° C.; adjusting the pH to 1.5 to 2.5; heating to 35° to 40° C.; adjusting the pH to 2.4 to 2.8 and then to 4.7 to 5.1; cooling to 15° to 25° C.; and recovering the cephradine hydrate obtained.

* * * * *